United States Patent
Radermacher et al.

(10) Patent No.: US 12,133,775 B2
(45) Date of Patent: Nov. 5, 2024

(54) ADAPTER FOR A ROBOTIC SURGICAL TOOL CLEANING SYSTEM

(71) Applicant: Cilag GmbH International, Zug (CH)

(72) Inventors: Ryne Derrick Radermacher, Liberty Township, OH (US); Mark Ronningen Burchnall, Cincinnati, OH (US); Bradley Jacob Sabo, Cincinnati, OH (US); Nicholas Martin Kloppenborg, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 1029 days.

(21) Appl. No.: 16/920,989

(22) Filed: Jul. 6, 2020

(65) Prior Publication Data

US 2021/0007828 A1 Jan. 14, 2021

Related U.S. Application Data

(60) Provisional application No. 62/871,963, filed on Jul. 9, 2019.

(51) Int. Cl.
*A61B 90/70* (2016.01)
*A61B 34/37* (2016.01)
*A61L 2/18* (2006.01)
*A61B 34/30* (2016.01)

(52) U.S. Cl.
CPC ............ *A61B 90/70* (2016.02); *A61B 34/37* (2016.02); *A61L 2/18* (2013.01); *A61B 2034/301* (2016.02); *A61B 2034/302* (2016.02); *A61L 2202/15* (2013.01); *A61L 2202/17* (2013.01); *A61L 2202/24* (2013.01)

(58) Field of Classification Search
CPC ..................................................... A61B 90/70
See application file for complete search history.

(56) References Cited

U.S. PATENT DOCUMENTS

2018/0168760 A1  6/2018  Koch, Jr. et al.

FOREIGN PATENT DOCUMENTS

| DE | 112012004786 T5 | 8/2014 |
|----|----|----|
| EP | 2701626 A1 | 11/2012 |
| EP | 2837352 A1 | 2/2015 |
| JP | 2002508219 A | 3/2002 |
| JP | 2007229493 A | 9/2007 |
| WO | 2015023772 A1 | 2/2015 |
| WO | 2018013314 A1 | 1/2018 |

OTHER PUBLICATIONS

European Search Report for EP Application No. 20184684.7 mailed Sep. 25, 2020.
Written Opinion and International Search Report for PCT/IB2020/056376 mailed Sep. 16, 2020.

*Primary Examiner* — Jason Y Ko

(57) ABSTRACT

An adapter for a robotic surgical tool autowasher system includes a frame matable with a drive housing of the robotic surgical tool, a shoulder defined on the frame and at least partially circumscribing a basin defined in the frame, and one or more fluid apertures defined in the basin and extending through the frame from a top surface to a bottom surface. One or more alignment features protrude from the frame and are arranged to align with and extend into a corresponding one or more apertures defined in a bottom of the drive housing. At least one of the one or more alignment features only partially plugs an associated aperture of the corresponding one or more apertures.

13 Claims, 5 Drawing Sheets

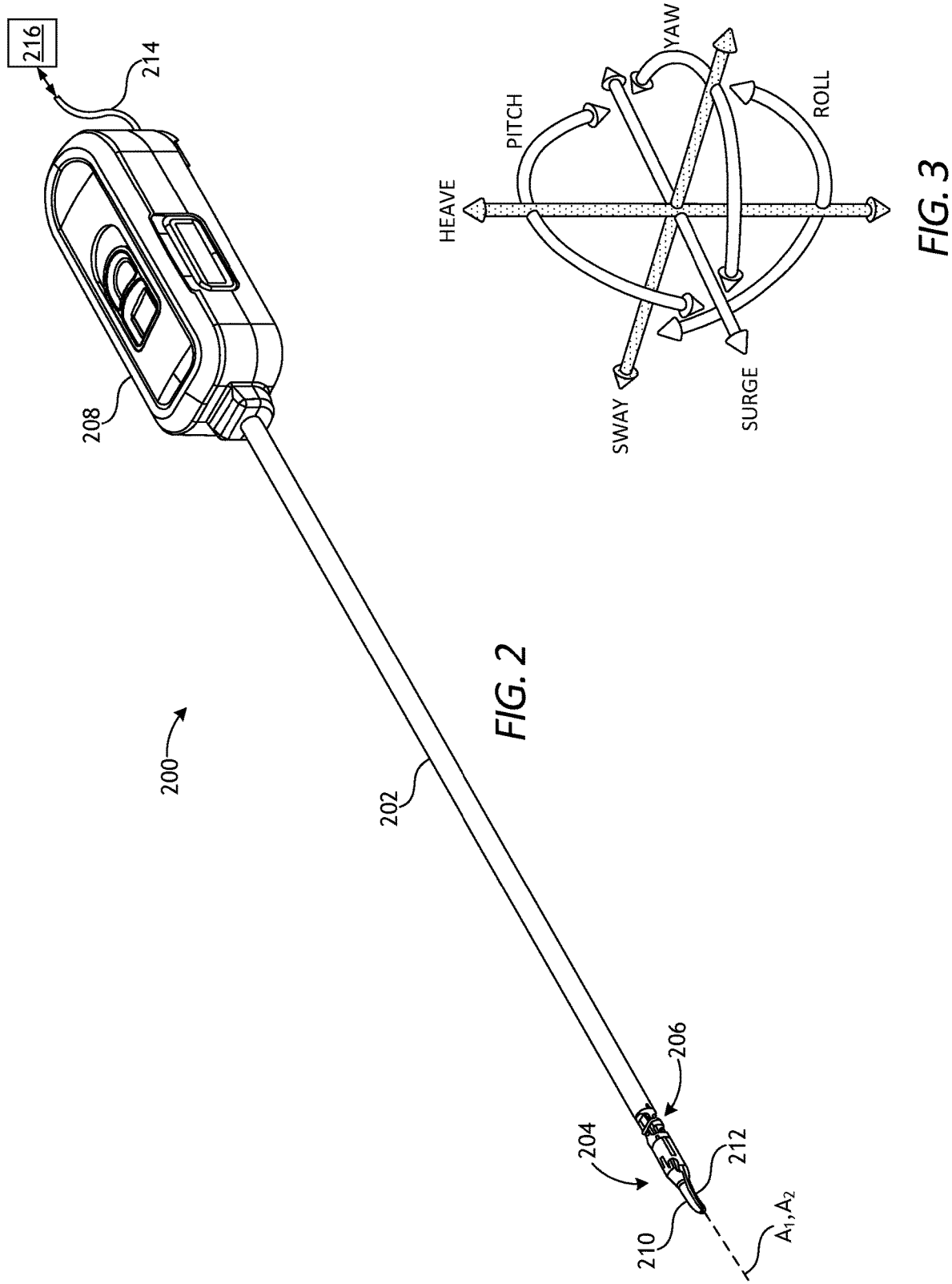

ADAPTER FOR A ROBOTIC SURGICAL TOOL CLEANING SYSTEM

BACKGROUND

Minimally invasive surgical (MIS) instruments are often preferred over traditional open surgical devices due to reduced post-operative recovery time and minimal scarring. Laparoscopic surgery is one type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity. The instruments and tools introduced into the abdominal cavity via the trocar can be used to engage and/or treat tissue in a number of ways to achieve a diagnostic or therapeutic effect.

Various robotic systems have recently been developed to assist in MIS procedures. Robotic systems can allow for more instinctive hand movements by maintaining natural eye-hand axis. Robotic systems can also allow for more degrees of freedom in movement by including an articulable "wrist" joint that creates a more natural hand-like articulation. In such systems, an end effector positioned at the distal end of the instrument can be articulated (moved) using a cable driven motion system having one or more drive cables (or other elongate members) that extend through the wrist joint. A user (e.g., a surgeon) is able to remotely operate the end effector by grasping and manipulating in space one or more controllers that communicate with a tool driver coupled to the surgical instrument. User inputs are processed by a computer system incorporated into the robotic surgical system, and the tool driver responds by actuating the cable driven motion system and thereby actively controlling the tension balance in the drive cables. Moving the drive cables articulates the end effector to desired angular positions and configurations.

Robotic surgical tools typically include a drive housing and a shaft that extends from the drive housing. The end effector is positioned at the end of the shaft and the wrist interposes the end effector and the end of the shaft to facilitate articulation of the end effector. The drive housing includes coupling features that releasably couples the surgical tool to a robotic surgical system, and houses various drive inputs and mechanisms (e.g., gears, actuators, etc.) designed to control operation of various features associated with the end effector.

After use, the drive housing and other component parts of the surgical tool must be fully cleaned and disinfected. Since proper and effective cleaning is vital for the health of patients, there is an ongoing need for improvements to the cleaning processes of robotic surgical tools.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIG. 2 is an isometric side view of an example surgical tool that may incorporate some or all of the principles of the present disclosure.

FIG. 3 illustrates potential degrees of freedom in which the wrist of the surgical tool of FIG. 2 may be able to articulate (pivot) or translate.

DETAILED DESCRIPTION

The present disclosure is related to robotic surgical systems and, more particularly, to adapters upon which a drive housing for a robotic surgical tool can be mounted for cleaning and disinfecting.

Embodiments disclosed herein describe an example adapter for a robotic surgical tool autowasher system. The adapter can include a frame matable with a drive housing of the robotic surgical tool, a shoulder defined on the frame and at least partially circumscribing a basin defined in the frame, and one or more fluid apertures defined in the basin and extending through the frame from a top surface to a bottom surface. One or more alignment features may protrude from the frame and are arranged to align with and extend into a corresponding one or more apertures defined in a bottom of the drive housing. At least one of the one or more alignment features only partially plugs an associated aperture of the corresponding one or more apertures.

Figure 1:
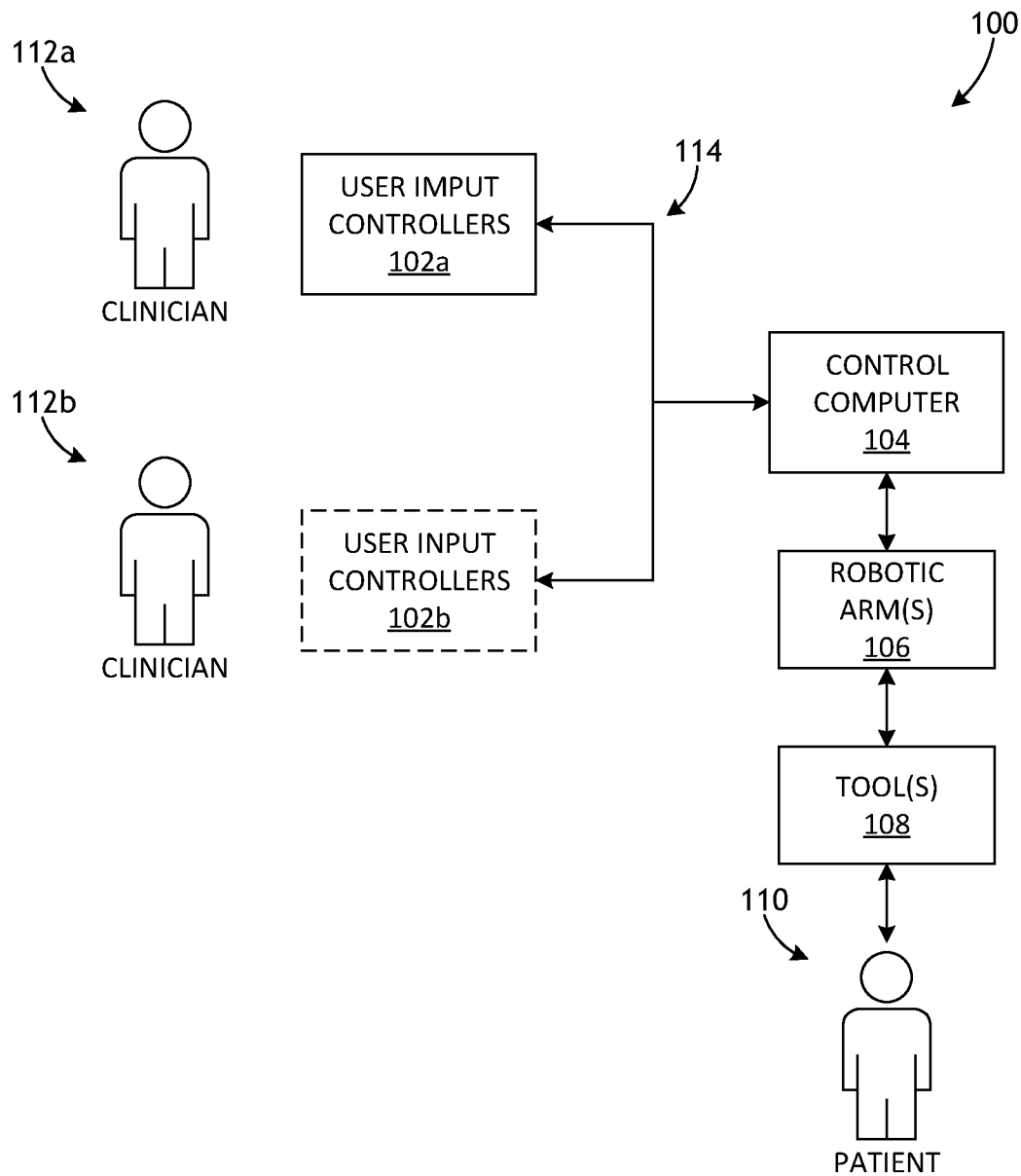
FIG. 1 is a block diagram of an example robotic surgical system that may incorporate some or all of the principles of the present disclosure.

FIG. 1 is a block diagram of an example robotic surgical system 100 that may incorporate some or all of the principles of the present disclosure. As illustrated, the system 100 can include at least one set of user input controllers 102a and at least one control computer 104. The control computer 104 may be mechanically and/or electrically coupled to a robotic manipulator and, more particularly, to one or more robotic arms 106 (alternately referred to as "tool drivers"). In some embodiments, the robotic manipulator may be included in or otherwise mounted to an arm cart capable of making the robotic surgical system 100 portable. Each robotic arm 106 may include and otherwise provide a location for mounting one or more surgical instruments or tools 108 for performing various surgical tasks on a patient 110. Operation of the robotic arms 106 and associated tools 108 may be directed by a clinician 112a (e.g., a surgeon) from the user input controller 102a.

In some embodiments, a second set of user input controllers 102b (shown in dashed lines) may be operated by a second clinician 112b to direct operation of the robotic arms 106 and tools 108 in conjunction with the first clinician 112a. In such embodiments, each clinician 112a,b may control different robotic arms 106 or, in some cases, complete control of the robotic arms 106 may be passed between the clinicians 112a,b. In some embodiments, additional robotic manipulators (not shown) having additional robotic arms (not shown) may be utilized during surgery on the patient 110, and the additional robotic arms may be controlled by one or more of the user input controllers 102a,b.

The control computer 104 and the user input controllers 102a,b may be in communication with one another via a communications link 114, which may be any type of wired or wireless telecommunications means configured to carry a variety of communication signals (e.g., electrical, optical, infrared, etc.) and according to any communications protocol.

The user input controllers 102a,b generally comprise one or more physical controllers that can be grasped or handled by the clinician 112a,b and manipulated in space while viewing the procedure via a stereo display. The physical controllers can comprise manual input devices movable in multiple degrees of freedom, and often include an actuatable handle or pedal for actuating the surgical tool(s) 108. The control computer 104 can also include an optional feedback meter viewable by the clinician 112a,b via a display to provide a visual indication of various surgical instrument metrics, such as the amount of force being applied to the surgical instrument (i.e., a cutting instrument or dynamic clamping member).

FIG. 2 is an isometric side view of an example surgical tool 200 that may incorporate some or all of the principles of the present disclosure. The surgical tool 200 may be the same as or similar to the surgical tool(s) 108 of FIG. 1 and, therefore, may be used in conjunction with a robotic surgical system, such as the robotic surgical system 100 of FIG. 1. In other embodiments, however, aspects of the surgical tool 200 may be adapted for use in a manual or hand-operated manner, without departing from the scope of the disclosure.

As illustrated, the surgical tool 200 includes an elongated shaft 202, an end effector 204, a wrist 206 (alternately referred to as a "wrist joint" or an "articulable wrist joint") that couples the end effector 204 to the distal end of the shaft 202, and a drive housing 208 coupled to the proximal end of the shaft 202. In robotic surgical systems, the drive housing 208 can include coupling features that releasably couple the surgical tool 200 to a robotic surgical system (e.g., the robotic arm 106 of FIG. 1).

The terms "proximal" and "distal" are defined herein relative to a robotic surgical system having an interface configured to mechanically and electrically couple the surgical tool 200 (e.g., the drive housing 208) to a robotic manipulator. The term "proximal" refers to the position of an element closer to the robotic manipulator and the term "distal" refers to the position of an element closer to the end effector 204 and thus further away from the robotic manipulator. Alternatively, in manual or hand-operated applications, the terms "proximal" and "distal" are defined herein relative to a user, such as a surgeon or clinician. The term "proximal" refers to the position of an element closer to the user and the term "distal" refers to the position of an element closer to the end effector 204 and thus further away from the user. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 200, the end effector 204 is configured to move (pivot) relative to the shaft 202 at the wrist 206 to position the end effector 204 at desired orientations and locations relative to a surgical site. To accomplish this, the drive housing 208 includes (contains) various drive inputs and mechanisms (e.g., gears, actuators, drive members, etc.) designed to control operation of various features associated with the end effector 204 (e.g., clamping, firing, rotation, articulation, cutting, etc.). In at least some applications, the shaft 202 and the end effector 204 coupled thereto are configured to rotate about a longitudinal axis $A_1$ of the shaft 202. In such embodiments, at least one of the drive inputs controls rotational movement of the shaft 202 about the longitudinal axis $A_1$.

The end effector 204 may comprise, but is not limited to, forceps, a grasper, a needle driver, scissors, an electro cautery tool, a vessel sealer, a stapler, a clip applier, a hook, a spatula, a suction tool, an irrigation tool, an imaging device (e.g., an endoscope or ultrasonic probe), or any combination thereof. In the illustrated embodiment, the end effector 204 comprises a tissue grasper and vessel sealer that includes opposing jaws 210, 212 configured to move (articulate) between open and closed positions. As will be appreciated, however, the opposing jaws 210, 212 may alternatively form part of other types of end effectors such as, but not limited to, surgical scissors, a clip applier, a needle driver, a babcock including a pair of opposed grasping jaws, bipolar jaws (e.g., bipolar Maryland grasper, forceps, a fenestrated grasper, etc.), etc. One or both of the jaws 210, 212 may be configured to pivot relative to the other to open and close the jaws 210, 212. The principles of the present disclosure, however, are equally applicable to end effectors without opposing jaws. In some embodiments, the surgical tool 200 may further be configured to apply energy to tissue, such as radio frequency (RF) energy.

FIG. 3 illustrates the potential degrees of freedom in which the wrist 206 may be able to articulate (pivot). The wrist 206 comprises a joint configured to allow pivoting movement of the end effector 204 relative to the shaft 202. The degrees of freedom of the wrist 206 are represented by three translational variables (i.e., surge, heave, and sway) and three rotational variables (i.e., Euler angles or roll, pitch, and yaw). The translational and rotational variables describe the position and orientation of the end effector 204 with respect to a given reference Cartesian frame. "Surge" refers to forward and backward translational movement, "heave" refers to translational movement up and down, and "sway" refers to translational movement left and right. "Roll" refers to tilting side to side, "pitch" refers to tilting forward and backward, and "yaw" refers to turning left and right.

The pivoting motion can include pitch movement about a first axis of the wrist 206 (e.g., X-axis), yaw movement about a second axis of the wrist 206 (e.g., Y-axis), and combinations thereof to allow for 360° rotational movement of the end effector 204 about the wrist 206. In other applications, the pivoting motion can be limited to movement in a single plane, e.g., only pitch movement about the first axis of the wrist 206 or only yaw movement about the second axis of the wrist 206, such that the end effector 204 moves only in a single plane.

Referring again to FIG. 2, the surgical tool 200 may also include a plurality of drive cables (obscured in FIG. 2) that form part of a cable driven motion system that facilitates movement and articulation of the end effector 204 relative to the shaft 202. Moving (actuating) the drive cables moves the end effector 204 between an unarticulated position and an articulated position. The end effector 204 is depicted in FIG. 2 in the unarticulated position where a longitudinal axis $A_2$ of the end effector 204 is substantially aligned with the longitudinal axis $A_1$ of the shaft 202, such that the end effector 204 is at a substantially zero angle relative to the shaft 202. In the articulated position, the longitudinal axes $A_1$, $A_2$ would be angularly offset from each other such that the end effector 204 is at a non-zero angle relative to the shaft 202.

In some embodiments, the surgical tool 200 may be supplied with electrical power (current) via a power cable 214 coupled to the drive housing 208. In other embodiments, the power cable 214 may be omitted and electrical power may be supplied to the surgical tool 200 via an internal power source, such as one or more batteries or fuel cells. In such embodiments, the surgical tool 200 may alternatively be characterized and otherwise referred to as an "electrosurgical instrument" capable of providing electrical energy to the end effector 204. The power cable 214 may place the surgical tool 200 in communication with a generator 216 that supplies energy, such as electrical energy (e.g., radio frequency energy), ultrasonic energy, microwave energy, heat energy, or any combination thereof, to the surgical tool 200 and, more particularly, to the end effector 204.

After the surgical tool 200 has been placed in service, it must be properly cleaned in preparation for future use. Because of the several moveable component parts contained within the drive housing 208, properly cleaning the internal components of the drive housing 208 can be a complex and time-consuming process. According to the present disclosure, various embodiments of adapters are disclosed that mechanically interface with the surgical tool 200 to couple the drive housing 208 to an autowasher system designed to fill the drive housing 208 with a cleaning and disinfecting solution, while simultaneously maintaining draining and drying capabilities.

Figure 4:
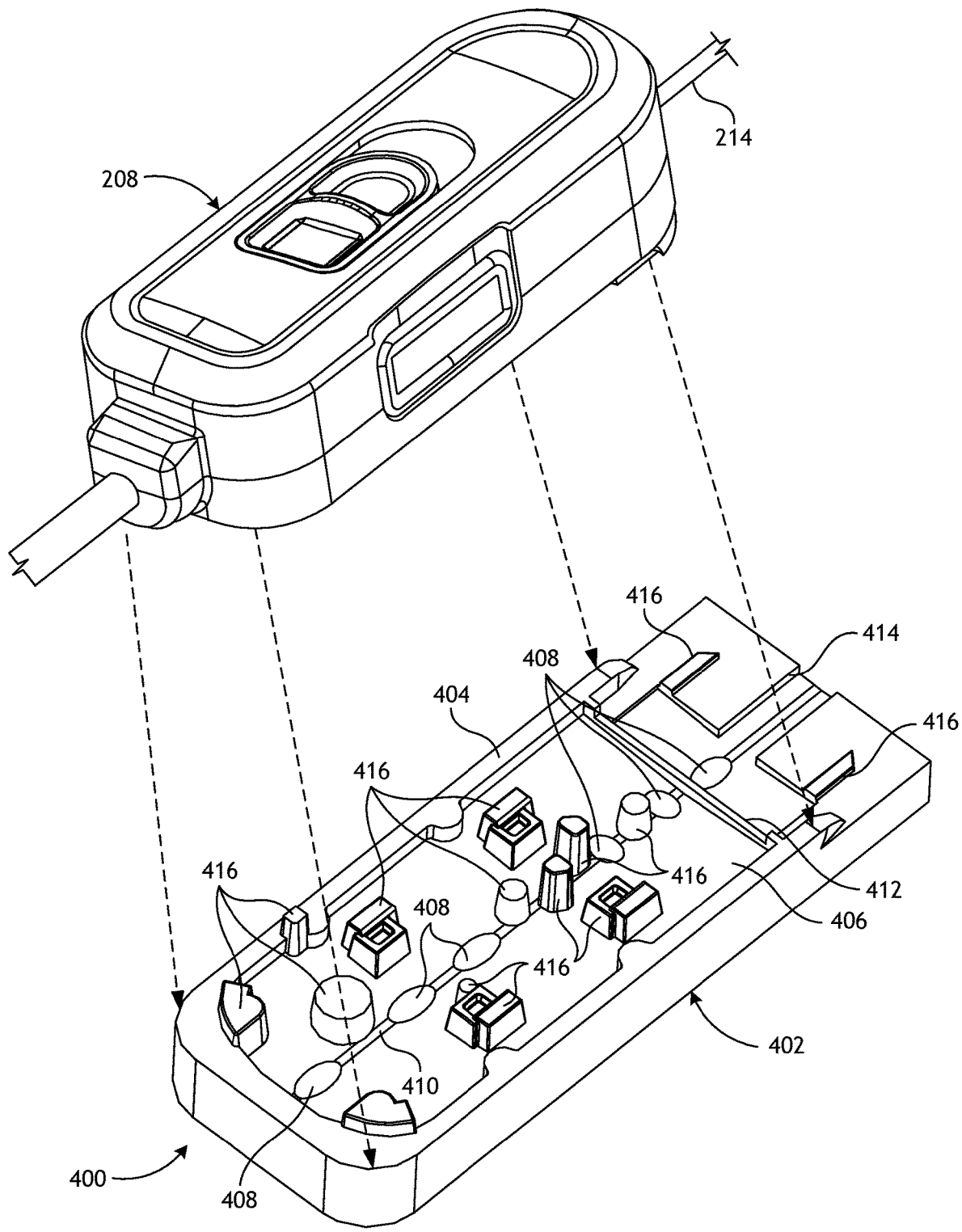
FIG. 4 is an isometric top view of an example adapter for a robotic surgical tool autowasher system, according to one or more embodiments.

FIG. 4 is an isometric top view of an example adapter 400 for a robotic surgical tool autowasher system, according to one or more embodiments. The adapter 400 may be sized and otherwise configured to receive and mate with the drive housing 208 to facilitate cleaning and disinfecting of the internal component parts of the drive housing 208 using the autowasher system. More specifically, the adapter 400 may be engageable or otherwise matable with the bottom of the drive housing 208. Once the drive housing 208 is properly mated to the adapter 400, the autowasher system may commence operation by injecting a cleaning and disinfecting solution (hereafter "the cleaning solution") into the interior of the drive housing 208 via the adapter 400. The cleaning solution may immerse or otherwise coat the internal components of the drive housing 208 and thereby help to clean and disinfect such internal parts. The cleaning solution may be flushed through the drive housing 208 and subsequently drained from the drive housing 208 via the adapter 400.

The cleaning solution used by the autowasher system may comprise any aqueous fluid configured to clean and disinfect the inner component parts of the drive housing. Example cleaning solutions include detergents such as, but are not limited to, Prolystica® 2X enzymatic detergent and Neodisher MediClean Forte.

As illustrated, the adapter 400 can include a generally rectangular frame 402 designed to generally match the size and shape of the bottom of the drive housing 208. In other embodiments, however, the size and shape of the frame 402 need not match the shape of the drive housing 208, without departing from the scope of the disclosure. The frame 402 may be made of a variety of rigid or semi-rigid materials including, but not limited to, a metal, a plastic, rubber, a composite material, or any combination thereof.

In some embodiments, as illustrated, the frame 402 may provide or otherwise define a shoulder 404 that extends continuously or non-continuously about some or all of the outer periphery of the frame 402. In the illustrated embodiment, the shoulder 404 provides a continuous rib feature that circumscribes portions of at least three sides of the frame 402. The shoulder 404 could alternatively extend about the entire periphery of the frame 402, or may otherwise be non-continuous about some or all of the periphery of the frame 402, without departing from the scope of the disclosure.

In some embodiments, the bottom of the drive housing 208 may be configured to engage or rest on the shoulder 404 when the drive housing 208 is properly mounted to the adapter 400. In other embodiments, or in addition thereto, the bottom of the drive housing 208 may be configured to mate with the shoulder 404 in an engagement that secures the drive housing 208 to the adapter 400, such as via an interference or snap fit engagement, or the like. The shoulder 404 may also be designed to help properly align the drive housing 208 with the adapter 400 and thereby help facilitate a mating engagement between the two structures. In such embodiments, a corresponding groove or channel (not shown) may be defined on the bottom of the drive housing 208 and the shoulder 404 may align with and be received in the groove to help align the drive housing 208 with the adapter 400.

As illustrated, the shoulder 404 protrudes outward a short distance from the upper surface of the adapter 400 and thereby helps define a basin 406 on the top surface of the frame 402. One or more fluid apertures 408 are defined in the basin 406 and extend through the frame 402 from the top surface to the bottom surface. While six fluid apertures 408 are shown in FIG. 4, more or less than six may be provided in the frame 402, without departing from the scope of the disclosure.

The fluid apertures 408 provide conduits for conveying the cleaning solution to and from the adapter 400 during cleaning operations. More specifically, the cleaning solution may be introduced to the basin 406 via the fluid apertures 408, and the adapter 400 may then convey the cleaning solution into the drive housing 208 mounted to the adapter 400. The fluid apertures 408 also provide drainage conduits that help drain used cleaning solution from the adapter 400 and the drive housing 208 after cleaning and disinfecting. In some embodiments, the fluid apertures 408 may further be used to help dry the internal components of the drive housing 208. In such embodiments, a gas (e.g., air or another dry gas) may be injected into the interior of the drive housing 208 via the fluid apertures 408. Continued injection of the gas will help dry internal components of the drive housing 208 and further flush out any cleaning solution that might remain within the interior.

In some embodiments, as illustrated, the bottom of the basin 406 may be tapered or angled toward a centerline 410 of the basin 406 and the fluid apertures 408 may be located at or near the centerline 410. Consequently, the basin 406 may promote fluid flow toward the centerline 410 and the fluid apertures 408 for draining used cleaning solution. In other embodiments, however, the bottom of the basin 406 may be flat, without departing from the scope of the disclosure.

In at least one embodiment, the frame 402 may further provide or define one or more fluid dams 412 (one shown) that transverse or extend at least partially across the basin 406. The fluid dam(s) 412 may help retain cleaning solution within the basin 406 during cleaning operations, but may also be configured to mate with corresponding features on the bottom of the drive housing 208 and thereby help properly align the drive housing 208 with the adapter 400.

In one or more embodiments, the frame 402 may further provide or define a channel 414 that may help facilitate additional drainage along with the fluid apertures. In at least one embodiment, as illustrated, the channel 414 may extend from the basin 406 along the centerline 410, but could alternatively be placed at any other location.

The adapter 400 may further provide or define one or more alignment features 416 that protrude from the upper surface of the frame 402. In some embodiments, as illustrated, one or more of the alignment features 416 may extend past the height of the shoulder 404. The alignment features 416 may be arranged on the frame 402 to align with and extend into corresponding apertures (orifices) defined in the bottom of the drive housing 208. In conjunction with the shoulder 404 (and the fluid dam 412), the design and placement of the alignment features 416 may help properly align the drive housing 208 (FIG. 2) onto the frame 402 for cleaning operations.

The apertures (orifices) defined in the bottom of the drive housing 208 may also facilitate fluid communication into the interior of the drive housing 208. Consequently, as the cleaning solution is introduced into the adapter 400, the cleaning solution will also migrate into and fill the interior of the drive housing 208 via such apertures (orifices). In some embodiments, however, one or more of the alignment features 416 may plug or seal the corresponding apertures (orifices) of the drive housing 208, which allows the adapter 400 to selectively limit the flow area into the drive housing 208, and thereby allow the drive housing 208 to properly fill with cleaning solution during cleaning operations. One or more other alignment features 416, however, may only partially plug (e.g., loosely occlude) the corresponding apertures of the drive housing 208, thereby allowing the cleaning solution to enter and drain from the drive housing 208 once the internal component parts are properly disinfected. As will be appreciated, this may yield improved cleanability, rinsing, and flushing in an autowasher as compared to a standalone tool.

The adapter 400 interfaces the drive housing 208 to the autowasher system. In operation, the drive housing 208 will be attached to the adapter 400 either before placement within the autowasher or the adapter 400 may otherwise be integral to the autowasher and the drive housing 208 would be attached when placed within the autowasher. The adapter 400 remains attached throughout the cleaning and disinfecting cycle. In some embodiments, the adapter 400 may be connected to autowasher flow supply lines. In the instances where the adapter 400 is integral to the autowasher, these connections may be permanent or semi-permanent. When the adapter 400 is a separate component, the autowasher flow supply lines would be detachable.

Figure 5:
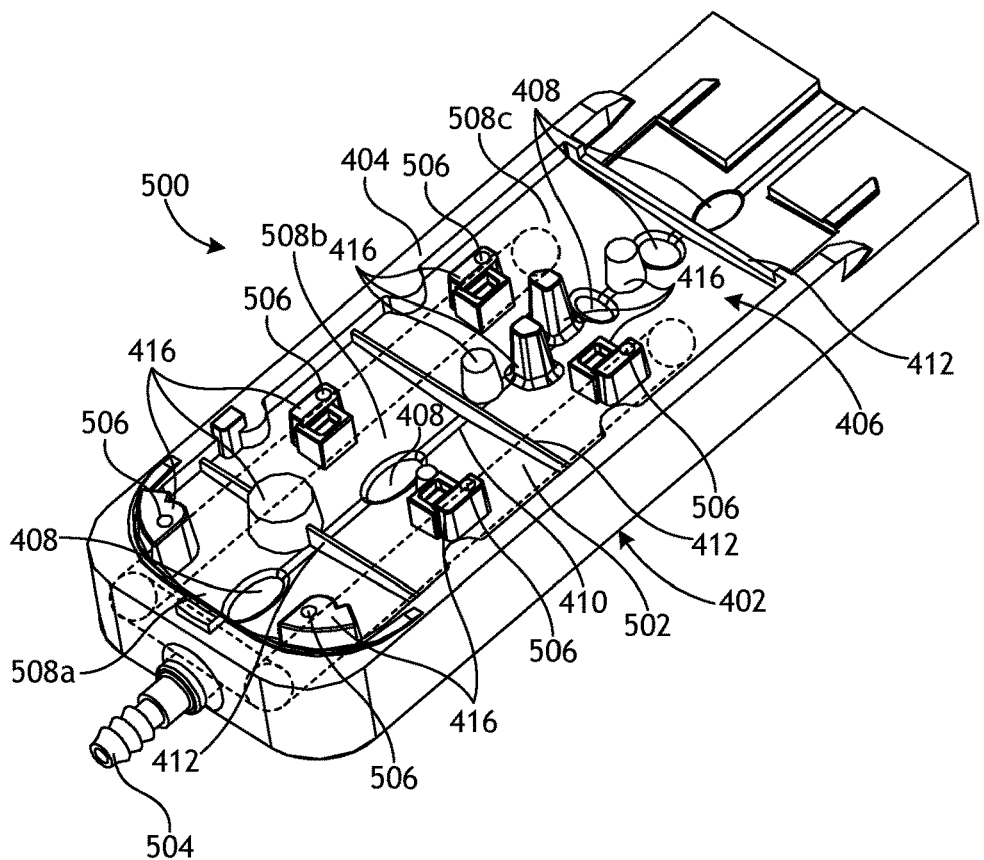
FIG. 5 is an isometric view of another example adapter for a robotic surgical tool autowasher system, according to one or more additional embodiments.

FIG. 5 is an isometric view of another example adapter 500 for a robotic surgical tool autowasher system, according to one or more additional embodiments. The adapter 500 may be similar in some respects to the adapter 400 of FIG. 4 and therefore may be best understood with reference thereto, where like numerals will represent like components not described again in detail. Similar to the adapter 400, for example, the adapter 500 includes the frame 402 matable with the drive housing 208 (FIG. 4) to facilitate cleaning and disinfection of the internal component parts of the drive housing 208 using the autowasher system. The adapter 500 also includes the shoulder 404 that helps define the basin 406 and may further help align the drive housing 208 with the adapter 500 for proper mating engagement. The fluid apertures 408 are defined in the basin 406 and extend through the frame 402 from the top surface to the bottom surface, and may be generally aligned with the centerline 410 to provide conduits for draining the cleaning solution from the adapter 500 during cleaning operations. The adapter 500 further provides the alignment features 416 protruding from the upper surface of the frame 402 and arranged on the frame 402 to align with and extend at least partially into corresponding apertures (orifices) defined in the bottom of the drive housing 208.

Unlike the adapter 400 of FIG. 4, however, the adapter 500 may include one or more internal conduits 502 (shown in dashed lines) defined in the frame 402 and a fitting 504 connected to the frame 402 and configured to fluidly connect the internal conduit(s) 502 to the autowasher system. Moreover, the internal conduit(s) 502 may be in fluid communication with one or more fluid nozzles or outlets 506 defined or otherwise provided in a corresponding one or more of the alignment features 416. In the illustrated embodiment, the internal conduit 502 extends from the fitting 504 and splits into two parallel channels that facilitate fluid communication with each fluid outlet 506. The fluid outlets 506 provide a discharge location for the cleaning solution to enter the interior of the drive housing 208 (FIG. 4). Moreover, while one or more of the alignment features 416 may plug or seal the corresponding apertures (orifices) of the drive housing 208, other alignment features 416 only partially plug (e.g., loosely occlude) the corresponding apertures of the drive housing 208, thus allowing the cleaning solution to drain from the drive housing 208.

In one example cleaning operation, the drive housing 208 (FIG. 4) may be mounted to the frame 402, as generally described above. The adapter 500 may then be placed in fluid communication with an autowasher system (not shown) by coupling a hose or other fluid conduit extending from the autowasher system to the fitting 504. A cleaning solution may then be introduced into the internal conduit(s) 502 from the autowasher system at the fitting 504, and the internal conduit(s) 502 convey the cleaning solution to each outlet 506. The cleaning solution is then ejected into the interior of the drive housing 208 via the outlets 506 to coat or immerse the internal components of the drive housing 208 with the cleaning solution and thereby clean and disinfect such parts. During and after the treatment, used cleaning solution may drain from the interior of the drive housing 208 via the alignment features 416 that only partially plug the corresponding apertures of the drive housing 208.

In some embodiments, the basin 406 may be divided into two or more fluid compartments. More specifically, the frame 402 may provide or define one or more fluid dams 412 (three shown) that transverse or extend at least partially across the basin 406. In the illustrated embodiment, the fluid dams 412 help form a first fluid compartment 508a, a second fluid compartment 508b, and a third fluid compartment 508c. At least one fluid aperture 408 is provided in each fluid compartment 508a-c to drain the used cleaning solution after draining from the interior of the drive housing 208 (FIG. 4).

In some embodiments, the fluid conduit(s) 502 may further be used to help dry the internal components of the drive housing 208 (FIG. 4). In such embodiments, a gas (e.g., air or another dry gas) may be injected into the adapter 500 via the fitting 504 and circulate through the fluid conduit(s) 502 and the outlets 506 to be discharged into the interior of the drive housing 208. Continued injection of the gas will help dry internal components of the drive housing 208 and further flush out any cleaning solution that might remain within the interior.

Figure 6A:
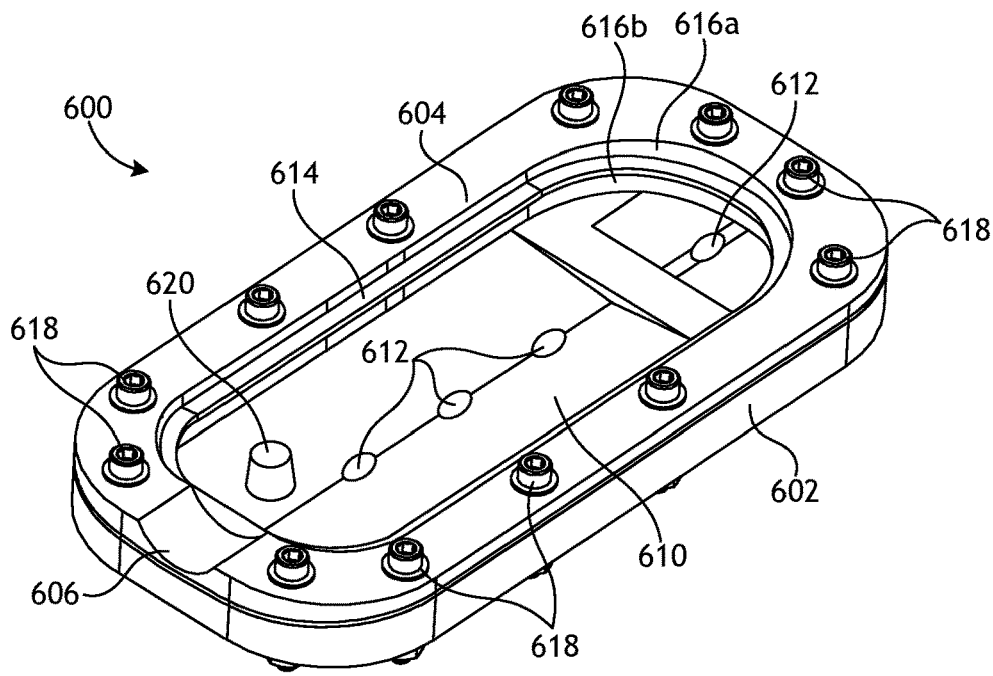
FIG. 6A is an isometric view of another example adapter for a robotic surgical tool autowasher system, according to one or more additional embodiments.
Figure 6B:
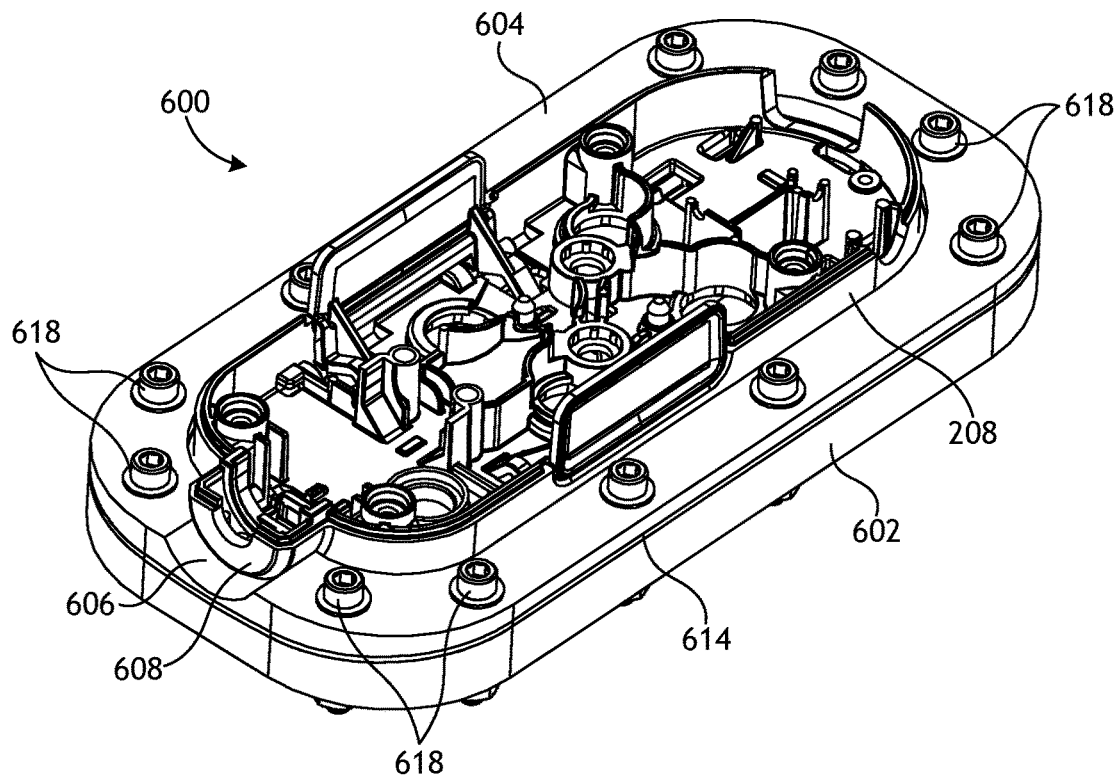
FIG. 6B depicts a portion of the drive housing mounted to the adapter of FIG. 6A, according to one or more additional embodiments.

FIG. 6A is an isometric view of another example adapter 600 for a robotic surgical tool autowasher system, and FIG. 6B depicts a portion of the drive housing 208 mounted to the adapter 600, according to one or more additional embodiments. The upper portion of the drive housing 208 and its internal parts are removed in FIG. 6B for simplicity. Similar to the adapters 400 and 500 of FIGS. 4 and 5, respectively, the adapter 600 may be matable with the drive housing 208 to facilitate cleaning and disinfection of the internal component parts of the drive housing 208 using the autowasher system. As illustrated, the adapter 600 includes a generally rectangular or pill-shaped frame 602. In some embodiments, the size and shape of the frame 602 may generally match that of the bottom of the drive housing 208. In other embodiments, however, the size and shape of the frame 602 need not match the shape of the drive housing 208, without departing from the scope of the disclosure. The frame 602 may be made of any of the materials mentioned above for the frame 402 of FIG. 4.

The frame 602 provides a shoulder 604 that extends continuously or non-continuously about all or a portion of the outer periphery of the frame 602. In the illustrated embodiment, the shoulder 604 provides a continuous rib that circumscribes the entire frame 602. The shape of the shoulder 604 may generally match the shape of the outer perimeter of the drive housing 208, and mounting the drive housing 208 to the adapter 600 may entail receiving the bottom of the drive housing 208 at the shoulder 604. In one or more embodiments, a channel or groove 606 may be defined within the frame 602 and, more particularly, within the shoulder 604 to accommodate one or more structural features of the drive housing 208. In the illustrated embodiment, the groove 606 is defined in the shoulder 604 and configured to accommodate a coupling feature 608 (FIG. 6B) forming part of the drive housing 208.

As best seen in FIG. 6A, the shoulder 604 helps define a basin 610 on the top surface of the frame 602, and one or more fluid apertures 612 are defined in the basin 610. While four fluid apertures 612 are shown in FIG. 6A, more or less than four may be provided in the frame 602, without departing from the scope of the disclosure. The fluid apertures 612 extend through the frame 602 from the top surface to the bottom surface, and provide conduits for conveying the cleaning solution to and from the adapter 600 during cleaning operations. More specifically, the cleaning solution may be introduced to the basin 610 via the fluid apertures 612, and the fluid apertures 612 may subsequently be used to drain used cleaning solution from the basin 610 after cleaning and disinfecting the drive housing 208.

In some embodiments, the adapter 600 may further include a gasket 614 positioned to engage and seal against the outer surface of the drive housing 208 when the drive housing 208 is mounted to the frame 602. The gasket 614 may provide a sealed interface against the outer surface of the drive housing 208 when the drive housing 208 is received within the basin 610 and thereby transform the basin 610 into a sealed region below the drive housing 208. In the illustrated embodiment, the gasket 614 extends inward from the shoulder 604 and into the basin 610 a short distance. In some embodiments, the gasket 614 may be coupled to or form an integral extension of the shoulder 604. In other embodiments, the shoulder 604 may comprise an upper portion 616a (FIG. 6A) matable with a lower portion 616b (FIG. 6A), and the gasket 614 may be secured to the frame 602 between the upper and lower portions 616a,b. In at least one embodiment, the upper and lower portions 616a,b may be secured together using one or more mechanical fasteners 618, but may alternatively be secured together by other means including, but not limited to, an adhesive, an interference fit, a snap fit engagement, or any combination thereof.

As best seen in FIG. 6A, the adapter 600 may further provide or define one or more alignment features 620 (one shown) that protrude from the upper surface of the frame 602. The alignment features 620 may be similar in some respects to the alignment features 416 of FIG. 4. Similar to the alignment features 416 of FIG. 4, for example, the alignment features 620 may be arranged on the frame 602 to align with and extend at least partially into corresponding apertures (orifices) defined in the bottom of the drive housing 208. In conjunction with the shoulder 604, the design and placement of the alignment features 620 may help properly align the drive housing 208 (FIG. 6B) onto the frame 602 for cleaning operations. In some embodiments, one or more of the alignment features 620 may plug or seal corresponding apertures (orifices) of the drive housing 208, which allows the adapter 600 to selectively limit the flow area into the drive housing 208, and thereby allow the drive housing 208 to properly fill with cleaning solution during cleaning operations. One or more other alignment features 620, however, only partially plug (e.g., loosely occlude) the corresponding apertures of the drive housing 208, thereby allowing the cleaning solution to enter and drain from the drive housing 208 once the internal component parts are properly cleaned and disinfected.

Figure 6C:
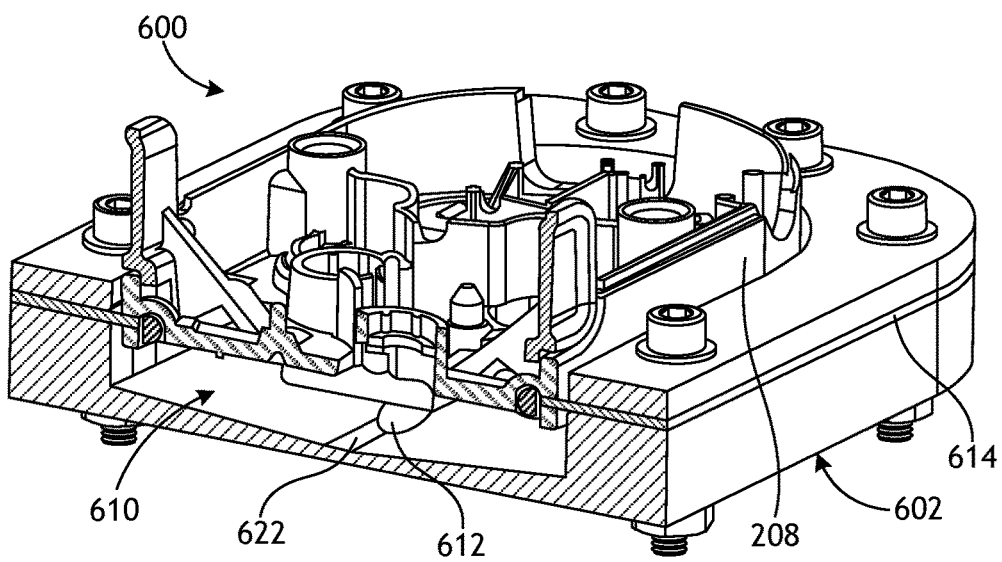
FIG. 6C is a cross-sectional side view of the adapter of FIGS. 6A-6C with the drive housing mounted thereto, according to one or more embodiments.

FIG. 6C is a cross-sectional side view of the adapter 600 with the drive housing 208 mounted thereto, according to one or more embodiments. As illustrated, the gasket 614 is positioned to engage and seal against the outer surface of the drive housing 208 when the drive housing 208 is mounted to the frame 602 and received within the basin 610. As the cleaning solution is introduced into the basin 610 via the fluid apertures 612, the gasket 614 forms a sealed interface that forces the cleaning solution to enter the drive housing 208 via the apertures (orifices) defined in the bottom of the drive housing 208. Accordingly, the gasket 614 forms a single seal around the outer perimeter of the drive housing 208 such that drainage out of the bottom of the adapter 600 is minimized, which allows the interior of the drive housing 208 to fill with the cleaning solution.

In some embodiments, as illustrated, the bottom of the basin 610 may be tapered or angled toward a centerline 622 of the basin 610 and the fluid apertures 612 may be located at or near the centerline 622. Consequently, the basin 406 may promote fluid flow toward the fluid apertures 612 for draining used cleaning solution. In other embodiments, however, the bottom of the basin 610 may be flat, without departing from the scope of the disclosure.

Referring now to FIGS. 6A-6C, in example cleaning operation the drive housing 208 (FIG. 6B) may be mounted to the frame 602 and the gasket 614 may form a seal about the outer perimeter of the drive housing 208, as generally described above. The adapter 600 may then be placed in fluid communication with an autowasher system (not shown) by coupling a hose or other conduit extending from the autowasher system to the fluid apertures 612. A cleaning solution may then be introduced into the basin 610 via the fluid apertures 612. Because of the sealed engagement facilitated by the gasket 614 between the drive housing 208 and the adapter 600, the cleaning solution may fill the sealed region and then proceed to enter the drive housing 208 via the one or more apertures (orifices) defined in the bottom of the drive housing 208. The cleaning solution may fill the drive housing 208 and thereby cover all internal surfaces and parts of the drive housing 208 with the cleaning solution. Used cleaning solution may then drain from the drive housing 208 and the adapter 600 through the fluid apertures 612. In some embodiments, the size of the fluid apertures 612 may allow the used cleaning solution to drain from the adapter 600 in a metered flow rate.

In some embodiments, the fluid apertures 612 may further be used to help dry the internal components of the drive housing 208. In such embodiments, a gas (e.g., air or another dry gas) may be injected into the interior of the drive housing 208 via the fluid apertures 612. Continued injection of the gas will help dry internal components of the drive housing 208 and further flush out any cleaning solution that might remain within the interior.

Embodiments disclosed herein include:

A. An adapter for a robotic surgical tool autowasher system that includes a frame matable with a drive housing of the robotic surgical tool, a shoulder defined on the frame and at least partially circumscribing a basin defined in the frame, one or more fluid apertures defined in the basin and extending through the frame from a top surface to a bottom surface, and one or more alignment features protruding from the frame and arranged to align with and extend into a corresponding one or more apertures defined in a bottom of the drive housing, wherein at least one of the one or more alignment features only partially plugs an associated aperture of the corresponding one or more apertures.

B. A method of cleaning a robotic surgical tool includes mating a drive housing of the robotic surgical tool with a frame of an adapter for an autowasher system, the frame including a shoulder defined on the frame and at least partially circumscribing a basin defined in the frame, and one or more fluid apertures defined in the basin and extending through the frame from a top surface to a bottom surface. The method further includes extending one or more alignment features protruding from the frame into a corresponding one or more apertures defined in a bottom of the drive housing and thereby aligning the drive housing with the frame, introducing a cleaning solution into an interior of the drive housing using the adapter, and draining the cleaning solution from the drive housing and the adapter via the one or more fluid apertures.

Each of embodiments A and B may have one or more of the following additional elements in any combination: Element 1: wherein the shoulder comprises a continuous or non-continuous rib that protrudes outward from an upper surface of the frame. Element 2: wherein the bottom of the drive housing rests on the shoulder when the drive housing is properly mounted to the adapter. Element 3: wherein used cleaning solution is drained from the basin via the one or more fluid apertures. Element 4: wherein a cleaning solution is conveyed into the basin via the one or more fluid apertures. Element 5: wherein a gas is introduced into the interior of the drive housing via the one or more fluid apertures to dry internal components of the drive housing. Element 6: wherein a bottom of the basin is angled toward a centerline of the basin and the one or more fluid apertures are located at the centerline. Element 7: further comprising one or more fluid dams that transverse the basin. Element 8: further comprising one or more internal conduits defined in the frame, a fitting connected to the frame and in fluid communication with the one or more internal conduits, and a fluid outlet defined in at least one of the one or more alignment features and in fluid communication with the one or more internal conduits, wherein a cleaning solution is introduced into an interior of the drive housing via the fluid outlet. Element 9: wherein a gas is introduced into the interior of the drive housing via the fluid outlet to dry internal components of the drive housing. Element 10: further comprising a gasket coupled to the shoulder and extending into the basin to engage and seal against an outer surface of the drive housing. Element 11: wherein the gasket is positioned above a top surface of the basin extends about an entire periphery of the basin. Element 12: wherein the shoulder comprises an upper portion separable from a lower portion, and wherein the gasket is secured to the frame between the upper and lower portions.

Element 13: wherein draining the cleaning solution from the drive housing comprises draining the cleaning solution pas at least one of the one or more alignment features that only partially plugs an associated aperture of the corresponding one or more apertures. Element 14: wherein introducing the cleaning solution interior of the drive housing comprises conveying the cleaning solution into the basin via the one or more fluid apertures, and flowing the cleaning solution into the interior of the drive housing from the basin via the one or more apertures defined in the bottom of the drive housing. Element 15: further comprising introducing a gas into an interior of the drive housing via the one or more fluid apertures and the one or more apertures defined in the bottom of the drive housing, and drying internal components of the drive housing with the gas. Element 16: wherein introducing the cleaning solution into the interior of the drive housing comprises conveying the cleaning solution into one or more internal conduits defined in the frame via a fitting connected to the frame and in fluid communication with the one or more internal conduits, and discharging the cleaning solution from the one or more internal conduits and into the interior of the drive housing via a fluid outlet defined in at least one of the one or more alignment features and in fluid communication with the one or more internal conduits. Element 17: further comprising introducing a gas into an interior of the drive housing via the fluid outlet, and drying internal components of the drive housing with the gas. Element 18: wherein the frame further includes a gasket coupled to the shoulder and extending into the basin, and wherein mating the drive housing with the frame comprises sealingly engaging an outer surface of the drive housing with the gasket.

By way of non-limiting example, exemplary combinations applicable to A, B, and C include: Element 3 with Element 4; Element 8 with Element 9; Element 10 with Element 11; Element 10 with Element 12; and Element 16 with Element 16.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. An adapter for a robotic surgical tool autowasher system, comprising:
   a frame matable with a drive housing of the robotic surgical tool;
   a shoulder defined on the frame and at least partially circumscribing a basin defined in the frame;
   one or more fluid apertures defined in the basin and extending through the frame from a top surface to a bottom surface; and
   one or more alignment features protruding from the frame and arranged to align with and extend into a corresponding one or more apertures defined in a bottom of the drive housing,
   wherein at least one of the one or more alignment features only partially plugs an associated aperture of the corresponding one or more apertures.

2. The adapter of claim 1, wherein the shoulder comprises a continuous or non-continuous rib that protrudes outward from an upper surface of the frame.

3. The adapter of claim 1, wherein the bottom of the drive housing rests on the shoulder when the drive housing is properly mounted to the adapter.

4. The adapter of claim 1, wherein used cleaning solution is drained from the basin via the one or more fluid apertures.

5. The adapter of claim 4, wherein a cleaning solution is conveyed into the basin via the one or more fluid apertures.

6. The adapter of claim 1, wherein a gas is introduced into the interior of the drive housing via the one or more fluid apertures to dry internal components of the drive housing.

7. The adapter of claim 1, wherein a bottom of the basin is angled toward a centerline of the basin and the one or more fluid apertures are located at the centerline.

8. The adapter of claim 1, further comprising one or more fluid dams that transverse the basin.

9. The adapter of claim 1, further comprising:
   one or more internal conduits defined in the frame;
   a fitting connected to the frame and in fluid communication with the one or more internal conduits; and
   a fluid outlet defined in at least one of the one or more alignment features and in fluid communication with the one or more internal conduits,
   wherein a cleaning solution is introduced into an interior of the drive housing via the fluid outlet.

10. The adapter of claim 9, wherein a gas is introduced into the interior of the drive housing via the fluid outlet to dry internal components of the drive housing.

11. The adapter of claim 1, further comprising a gasket coupled to the shoulder and extending into the basin to engage and seal against an outer surface of the drive housing.

12. The adapter of claim 11, wherein the gasket is positioned above a top surface of the basin extends about an entire periphery of the basin.

13. The adapter of claim 11, wherein the shoulder comprises an upper portion separable from a lower portion, and wherein the gasket is secured to the frame between the upper and lower portions.

* * * * *